United States Patent
Lauritsch et al.

(10) Patent No.: US 9,633,454 B2
(45) Date of Patent: Apr. 25, 2017

(54) FLUID-DYNAMIC ANALYSIS OF A VASCULAR TREE USING ANGIOGRAPHY

(71) Applicants: Günter Lauritsch, Nürnberg (DE); Thomas Redel, Poxdorf (DE); Michael Scheuering, Nürnberg (DE); Chris Schwemmer, Forchheim (DE)

(72) Inventors: Günter Lauritsch, Nürnberg (DE); Thomas Redel, Poxdorf (DE); Michael Scheuering, Nürnberg (DE); Chris Schwemmer, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/729,961

(22) Filed: Jun. 3, 2015

(65) Prior Publication Data
US 2015/0356753 A1 Dec. 10, 2015

(30) Foreign Application Priority Data
Jun. 4, 2014 (DE) .................. 10 2014 210 591

(51) Int. Cl.
*G06K 9/00* (2006.01)
*G06T 11/00* (2006.01)
(Continued)

(52) U.S. Cl.
CPC .......... *G06T 11/003* (2013.01); *A61B 6/4441* (2013.01); *A61B 6/486* (2013.01);
(Continued)

(58) Field of Classification Search
USPC ........ 382/100, 103, 106–107, 128–134, 154, 382/162, 168, 173, 181, 199, 219, 232,
(Continued)

(56) References Cited

U.S. PATENT DOCUMENTS

| 6,236,878 B1 | 5/2001 | Taylor et al. |
| 8,200,466 B2 | 6/2012 | Spilker et al. |

(Continued)

FOREIGN PATENT DOCUMENTS

| DE | 102010022791 A1 | 12/2011 |
| DE | 102010039312 A1 | 2/2012 |

(Continued)

OTHER PUBLICATIONS

Schwemmer CH. et al., "Opening Windows—Increasing Window Size in Motion-Compensated ECG-gated Cardiac Vasculature Reconstruction," Proceedings of the 12th International Meeting on Fully Three-Dimensional Image Reconstruction in Radiology and Nuclear Medicine, Jun. 16-21, Granlibakken Resort, Lake Tahoe, California, pp. 50-53, 2013.
(Continued)

*Primary Examiner* — Seyed Azarian
(74) *Attorney, Agent, or Firm* — Lempia Summerfield Katz LLC

(57) ABSTRACT

A method for ascertaining a fluid-dynamic characteristic value of a resilient vascular tree, through which a fluid flows in a pulsating manner, is provided. At least one 2D projection, respectively, of the resilient vascular tree is generated by a projection device from different angles of projection, and a digital 3D reconstruction of the vascular tree is generated by an analysis device based on of the 2D projections. A geometry of at least one vessel of the resilient vascular tree is estimated based on the 3D reconstruction, and at least one fluid state in the resilient vascular tree is ascertained from the geometry and predetermined resilient properties of the resilient vascular tree. The at least one fluid-dynamic characteristic value is calculated as a function of the at least one fluid state.

17 Claims, 3 Drawing Sheets

(51) Int. Cl.
*A61B 6/00* (2006.01)
*G06T 7/00* (2017.01)
*G06T 7/20* (2017.01)
*G06T 15/08* (2011.01)
*A61B 5/05* (2006.01)

(52) U.S. Cl.
CPC .............. *A61B 6/504* (2013.01); *A61B 6/507* (2013.01); *A61B 6/5235* (2013.01); *A61B 6/5264* (2013.01); *G06T 7/004* (2013.01); *G06T 7/0016* (2013.01); *G06T 7/20* (2013.01); *G06T 15/08* (2013.01); *A61B 6/481* (2013.01); *G06T 2207/10016* (2013.01); *G06T 2207/10028* (2013.01); *G06T 2207/10081* (2013.01); *G06T 2207/10116* (2013.01); *G06T 2207/30101* (2013.01); *G06T 2207/30104* (2013.01); *G06T 2211/404* (2013.01)

(58) Field of Classification Search
USPC ....... 382/254, 274, 276, 285–296, 305, 312; 600/431, 419; 345/419
See application file for complete search history.

(56) References Cited

U.S. PATENT DOCUMENTS

| | | | |
|---|---|---|---|
| 8,311,748 B2 | 11/2012 | Taylor et al. | |
| 8,315,812 B2 | 11/2012 | Taylor | |
| 8,315,821 B2 | 11/2012 | Brujic et al. | |
| 8,321,150 B2 | 11/2012 | Taylor | |
| 8,321,152 B2 | 11/2012 | Karlsson et al. | |
| 2011/0037761 A1* | 2/2011 | Mistretta | A61B 6/4441 345/419 |
| 2011/0298793 A1* | 12/2011 | Lauritsch | A61B 6/504 345/419 |
| 2012/0041301 A1 | 2/2012 | Redel | |
| 2012/0280978 A1* | 11/2012 | Holub | A61B 5/0044 345/419 |
| 2013/0237815 A1* | 9/2013 | Klingenbeck | A61B 6/4441 600/431 |
| 2014/0024932 A1* | 1/2014 | Sharma | A61B 6/507 600/431 |

FOREIGN PATENT DOCUMENTS

| | | |
|---|---|---|
| DE | 102010062975 A1 | 6/2012 |
| EP | 2242023 B1 | 1/2012 |

OTHER PUBLICATIONS

Schwmmer, C., et.al.: "Residual motion compensation in ECG-gated interventional cardiac vasculature reconstruction," in: Phys. Med. Biol., vol. 58, pp. 3717-3737, 2013.

Taylor CH. A. et al, "Computational Fluid Dynamics Applied to Cardiac Computed Tomography for Noninvasive Quantification of Fractional Flow Reserve—Scientific Basis," Journal of the American College of Cardiology (JACC), vol. 61, No. 22, pp. 2233-2241, 2013.

German Office action for related German Application No. 10 2014 210 591.9, with English Translation, mailed Feb. 2, 2015.

* cited by examiner

FLUID-DYNAMIC ANALYSIS OF A VASCULAR TREE USING ANGIOGRAPHY

This application claims the benefit of DE 10 2014 210 591.9, filed on Jun. 4, 2014, which is hereby incorporated by reference in its entirety.

BACKGROUND

The present embodiments relate to ascertaining a fluid-dynamic characteristic value of a resilient vascular tree through which a fluid flows in a pulsating manner.

The vascular tree may be, for example, coronary arteries of a heart of a person or animal. Coronary heart disease is one of the most common and expensive disease patterns with a dramatic course. Stent implantation has proven itself as a treatment for coronary heart disease. Stent implantation is one of the most common therapies and is performed in the cardiac catheterization laboratory. In this way, constrictions (e.g., stenoses) may be widened or at least stabilized. The effect of a stenosis, and therewith the need for the stenosis to be treated, depends, however, not just on the extent of the constriction, but also on the size of the subsequent perfusion area. Similar degrees of stenosis may therefore necessitate different therapeutic treatment strategies. Treatment of a hemodynamically harmless stenosis is of no advantage to the patient, so treatment may be abstained owing to the risk of a stent implantation.

To be able to decide about a treatment, a hemodynamic characteristic value of the vascular tree constricted by the stenosis is to be ascertained. Various, supplementary examination methods that may provide information about the functional relevance of a stenosis have therefore been introduced. A hemodynamic characteristic value of this kind is the fractional flow reserve. The drop in pressure over the stenosis is ascertained in this connection using a pressure level measurement. In this method, the mean pressure is to be measured proximally and distally of the stenosis with maximum blood flow, and is to be related. If the value drops below a certain threshold value, a hemodynamically significant stenosis may be assumed. One drawback of this method is that the method is catheter based (e.g., is invasive). With maximum vasodilatation, something that may be achieved by administering adenosine, the measurement brings an additional burden for the patient.

It is known from U.S. Pat. No. 8,311,748 B2, U.S. Pat. No. 8,315,821 B2 and U.S. Pat. No. 8,321,152 B2 that a model of a vascular tree that is to be analyzed hemodynamically may be generated based on 3D image data of a computer tomograph (CT), a magnetic resonance tomograph (MRT), or a proton emission computer tomograph (PET), and may be carried out using the model computer-based fluid-dynamic calculations (Computational fluid Dynamics (CFD)). In a scientific study by Taylor et al. (Charles A. Taylor, Timothy A. Fonte, James K. Min, "Computational Fluid Dynamics Applied to Cardiac Computed Tomography for Noninvasive Quantification of Fractional Flow Reserve," Journal of American College of Cardiology, published by Elsevier Inc, 2013) it was found, however, that, when generating such 3D image data using a computer tomograph, artifacts that affect the validity of a computer-based calculated FFR value are produced in the model of the vascular tree.

The reason for the artifacts is the aggravated recording condition that during execution of computer tomography blood flows through the examined vascular tree in a pulsating manner in time with the heartbeat, and the resilient walls of the vessels deform as a result.

An adaptive method for CFD calculation by which differences in a cardiovascular model from the underlying image data are compensated is known from U.S. Pat. No. 8,200,466 B2. In this method, the complexity of the cardiovascular model (e.g., the computing effort for this model) increases all the more, the more movement artifacts the underlying image material has.

In connection with cardiovascular models, a method for simulating an operation based on a model of this kind is known from U.S. Pat. No. 6,236,878 B1. The significance of a simulation of this kind depends on the quality of the model. The model is generated based on CT data or MR data in the document.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a fluid-dynamic characteristic value is ascertained for a vascular tree based on image data of the vascular tree.

The method of one or more of the present embodiments starts from a vascular tree that is resilient and through which a fluid flows in a pulsating manner. A vascular tree, for example, which is supplied with blood, may therefore be examined using the method. For example, a vascular tree including coronary arteries may be examined. The method of one or more of the present embodiments is also suitable, however, for examining other materials through which fluid flows.

In the method, at least one 2D projection, respectively, of the vascular tree is generated by a projection device (e.g., an angiography system) from different angles of projection. A C-arm angiography system, for example, may be used as the projection device, as may be obtained with the product name "DynaCT"® belonging to Siemens AG®. The 2D projections are transmitted to an analysis device as 2D projection image data. The analysis device generates a digital 3D reconstruction of the vascular tree based on the 2D projections. A method that is known may be used (e.g., filtered back projection). A geometry of at least one vessel of the vascular tree (e.g., a diameter of the vessel) is estimated based on the 3D reconstruction. At least one fluid state in the vascular tree (e.g., the pressure of the fluid at a specific instant or a flow rate) is ascertained from the geometry and predetermined resilient properties of the vascular tree. The at least one desired fluid-dynamic characteristic value is then calculated (e.g., a characteristic value of the vascular tree that describes the fluid dynamics) as a function of the at least one fluid state.

The method of one or more of the present embodiments has the advantage that geometric data of at least one vessel, which is ascertained based on 2D projections of the vascular tree, is used for the calculation of the at least one fluid-dynamic characteristic value, so the vascular tree is depicted more sharply. A more precise estimate of the geometry and therewith a more accurate calculation of the at least one fluid-dynamic characteristic value may also be achieved thereby. Two-dimensional projection data of this kind is not available in conventional computer tomographs.

In connection with the fluid-dynamic analysis of a vascular tree (e.g., a hemodynamic analysis), use of a C-arm angiography system has the advantage that the C-arm angiography system may also be used in the described cardiac catheterization laboratory, so a patient may be both positioned there for the hemodynamic analysis and be prepared for a stent implantation. Relocation of the patient and the time delay associated therewith is to be accepted in the case of hemodynamic analysis based on CT image data.

To also obtain a 3D reconstruction with a low proportion of movement artifacts from the sharper images of the 2D projections, a movement-compensated reconstruction may be carried out, as is known by way of example from the two specialist articles by Schwemmer et al. (C. Schwemmer, C. Rohkohl, G. Lauritsch, K. Müller, J. Hornegger, "Residual motion compensation in ECG-gated interventional cardiac vascular reconstruction," Institute of Physics and Engineering in Medicine and Biology, Phy. Med. Biol., 58, pages 3717-37, 2013; and "Opening Windows—Increasing Window Size in Motion-Compensated ECG-gated Cardiac Vascular Reconstruction," 12th International Meeting on Fully Three-Dimensional Image Reconstruction in Radiology and Nuclear Medicine, Viterbi School of Engineering, University of Southern California, 2013), which are hereby incorporated by reference in their entirety. The 3D reconstruction may be provided, for example, as a 3D image data record that indicates a tissue property or material property (e.g., a Hounsfield Unit (HU) value) of the vascular tree, for individual voxels.

Using the 3D reconstruction, the at least one vessel, for example, may then be segmented using threshold values, and then, a distinction may be made in the vessel between vessel walls and the fluid. From this, for example, the internal diameter of the at least one vessel may be estimated as geometry of the vessel. An estimate may be, for example, that it is being assumed that the exact value of the vessel is not the issue. Since for the resilient vessel a resilient property of the resilient vessel may be ascertained in advance (e.g., using examinations of other vessels of the same type), a conclusion may be drawn about the fluid state in the at least one vessel from the geometry and the resilient properties. By way of example, the fluid volume and/or a respective fluid pressure at two different instants at least may be ascertained, and this may be discerned, for example, from a change in diameter. In addition or alternatively, a respective fluid pressure may be ascertained at two different locations at least in the vascular tree. A change in pressure, for example, may be ascertained herefrom, as is required for calculating the FFR value.

For the case where in the 3D reconstruction movement artifacts make ascertaining the geometry of the at least one vessel difficult, one or more of the present embodiments provide a plurality of advantageous developments to compensate the movement artifacts.

According to one development, one 3D route, respectively, of the at least one vessel (e.g., a 3D center line) is ascertained to estimate the geometry of the at least one vessel in the 3D reconstruction. The 3D route is projected onto one of the 2D projections. An edge of the at least one vessel is ascertained in the 2D projection starting from the projected 3D route. This edge is more sharply depicted in the 2D projection in the manner already described since there are no significant movement artifacts here. The edge is then projected back into the 3D construction. This results in the advantage that a movement artifact may be discerned and reduced or eliminated in the 3D reconstruction.

One development provides that the projected 3D route is not taken as the direct starting point. Instead, a 2D route of the at least one vessel is ascertained in the 2D projection, and the projected 3D line and the 2D route are registered in relation to each other. This results in the advantage that the pulse phase of the vascular tree shown in the 3D reconstruction (e.g., the instantaneous form of the resilient vascular tree) does not have to exactly match the pulse phase depicted in the 2D projection. A difference in the form due to the pulsating movement of the vascular tree is compensated by the registration.

The 3D route may be projected not just onto a single 2D projection, but onto at least one further 2D projection, and then, one edge respectively of the at least one vessel is also ascertained in each further 2D projection. Since the 2D projections may have been generated from different angles of projection, a profile line of the at least one vessel may then be ascertained based on all back-projected edges in the 3D reconstruction (e.g., a contour of the vessel in the cross-section). This results in a more accurate description of the geometry of the vessel, so the fluid state may be determined more accurately.

A further advantage results if the 2D projections, onto which the 3D route is projected, are not all generated at different pulse phases of the pulse cycle (e.g., at different phases of the heartbeat), and instead, the 2D reconstructions show the vascular tree at pulse phases that are as similar as possible. This provides that the 3D route is not just projected onto the 2D projections in which a difference in the pulse phases is smaller than a predetermined tolerance value. This advantageously prevents the diameter of the vessel from being overestimated. The pulse phase may be ascertained, for example, using an electrocardiogram (ECG) in the case of a living being.

If an accurate geometry of the at least one vessel of the vascular tree then exists, then, starting from the geometry, the at least one fluid state may advantageously be ascertained using a computational fluid-dynamics method (CFD). Due to the particularly sharply depicted edges of the vessels, as may be ascertained by the 2D projection, these methods, unlike in the prior art, may be reliably used to ascertain fluid states.

Further advantages result by checking further plausibility conditions. For this purpose, one development of the method provides that an estimate for a quantity of fluid flowing per pulse beat is ascertained on a different basis, and the quantity of fluid is used as a boundary condition for the CFD calculation. The quantity of fluid may be ascertained based on a volume and/or a mass of an organ supplied with the fluid via the vascular tree. By way of example, the supplied myocardial mass may therefore be ascertained during the examination of coronary arteries. Provision of these boundary conditions results in the advantage that incorrect or implausible solutions may be ruled out in the case of ambiguous solutions that may result with the CFD calculation.

A further possibility for more accurate determination of the fluid state results if an absolute fluid pressure value is ascertained in the vascular tree and/or on a vessel that communicates fluidically with the vascular tree. This may be, for example, a blood pressure measurement. This results in the advantage that the fluid states that may be ascertained only on a relative basis in the 3D reconstruction may be converted into absolute values, and the details that are based on the absolute variables may hereby also be used in relation to the resilient properties.

If the geometry and the fluid states now exist, a large number of different fluid-dynamic characteristic values may be ascertained for the vascular tree. One embodiment of the method provides that a drop in pressure in the fluid caused by a vasoconstriction of the vascular tree is ascertained as the fluid-dynamic characteristic value. Alternatively or additionally, a value that correlates with a fractional flow reserve (e.g., describes this) may be ascertained. The actual fractional flow reserve may otherwise only be ascertained via an invasive pressure wire measurement.

The 3D reconstruction generated by the method of one or more of the present embodiments may, however, advantageously be used even further. One development of the method provides that a manipulation of the vascular tree is simulated in the 3D reconstruction (e.g., an implantation of a stent). Using the simulation, a manipulation-induced fluid-dynamic characteristic value is then predicted (e.g., the change in the fluid-dynamic characteristic value is predicted for a user). This results in the advantage of a doctor, for example, being able to plan an operation more effectively.

As already stated, a C-arm X-ray system may be used as a projection unit to be able to carry out the hemodynamic analysis of a vascular tree (e.g., of coronary vessels) interventionally (e.g., within the context of an operation or its preparation). For this purpose, one or more of the present embodiments provide a C-arm X-ray system with a projection unit that has an X-ray source for penetrating a vascular tree in a body and an X-ray detector for generating 2D projection data of 2D projections of the penetrated vascular tree. According to one or more of the present embodiments, an analysis device for ascertaining at least one fluid-dynamic characteristic value based on the 2D projections is provided in the C-arm X-ray system (e.g., a processor, a computer, or a Digital Signal Processor (DSP)), and the C-arm X-ray system is configured to carry out an embodiment of the method.

DETAILED DESCRIPTION

In the exemplary embodiments, the described components each represent individual features that are to be considered independently of each other. The present embodiments develop the described components independently of each other in each case and are therefore also to be regarded as part of the present embodiments individually or in a combination other than that shown. The described embodiments may also be supplemented by more of the features of the present embodiments that have already been described.

Figure 1:
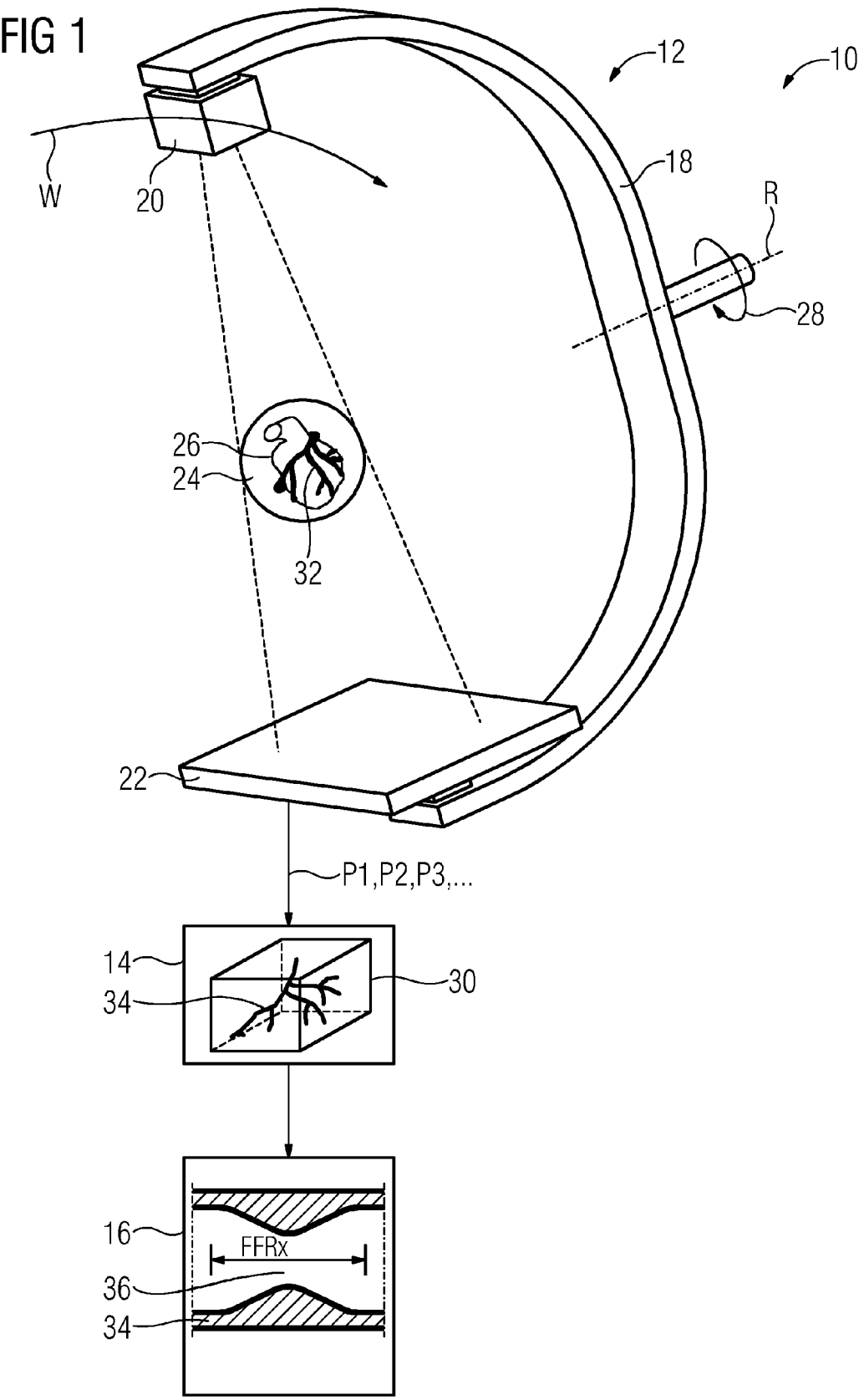
FIG. 1 shows a schematic view of an embodiment of a C-arm X-ray system.

FIG. 1 shows an embodiment of a C-arm angiography system or angiograph 10 that may include a C-arm X-ray system 12, an analysis device 14, and a display device 16 (e.g., a screen). The angiograph 10 may be provided, for example, in a catheterization laboratory for the examination of infarct patients.

The C-arm X-ray system 12 may include a C-arm 18 that is mounted so as to rotate about an axis of rotation R. An X-ray source 20 may be arranged on the C-arm 18 at one end of the C-arm, and an X-ray detector 22 (e.g., an X-ray flat panel detector) may be arranged on the C-arm 18 at the opposing end of the C-arm 18. The analysis device 14 may be, for example, a processor (e.g., a digital computer or computer). The display device 16 may be implemented, for example, by a screen. The angiograph 10 may be based, for example, on the system DynaCT already described, which may be developed according to one or more of the present embodiments.

A body of a patient, for example, may be examined using the angiograph 10. In the illustrated example, the thorax 24 of the patient with a heart 26 located therein is shown for the purpose of illustration. The penetrated object may, however, also originate from the non-human field. For example, components or materials or chemicals may be penetrated and displayed.

Using the C-arm X-ray system 12, one X-ray image, respectively, may be obtained from different directions or angles of projection by operating the X-ray source 20 and receiving the projection of the thorax 24 using the X-ray detector 22. For this purpose, the C-arm 18 may be rotated to move the X-ray source 20 along a route or a trajectory W and to control the angle of projection about the axis of rotation R in a rotational movement 28 in a desired angular interval of, for example, 0 degrees to 200 degrees, and a respective recording of the thorax 24 may be generated at the appropriate angular positions.

With each recording, the X-ray detector 22 generates respective 2D x-ray image data of the 2D projections P1, P2, P3 (and further 2D projections that are not shown), which are transmitted to the analysis device 24. The recordings (e.g., the 2D projections P1, P2, P3 and the x-ray image data generated for the further angles of projection) are combined by the analysis device 24 into a 3D volume model 30 that, for individual volume elements of the thorax 24, indicates, for example, an absorption property or attenuation property with respect to the X-ray radiation of the X-ray source 20. A unit for an attenuation value of this kind is, for example, Hounsfield Unit (HU).

In the illustrated example, a vascular tree 32 of the heart 26 (e.g., the coronary vessels of one side of the heart) is to be examined. The volume model 30 has a 3D reconstruction 34 of the vascular tree 32. A stenosis 36, for example, may be located in the vascular tree 32, for which a hemodynamic characteristic value FFRx is to be non-invasively ascertained by the analysis device using the volume model 30. The characteristic value FFRx may be, for example, an FFR value ascertained based on a computer. The characteristic value FFRx may be displayed to a user (not shown) of the angiograph 10 (e.g., using the display device 16).

An FFR-correlated value FFRx of this kind has previously been calculated by recordings of the heart 26 in computer tomography. This has the advantage that neither catheter measurement nor the administration of adenosine is necessary. Since, however, computer tomographs may not be provided in a cardiac catheterization laboratory, the aim with the angiograph 10 is to select patients even before the cardiac catheterization examination and therefore save this expensive invasive examination for patients with functional, non-relevant stenoses. Previously, a patient therefore firstly was placed in a computer tomograph in order to be able to decide whether the patient should be transferred into the cardiac catheterization laboratory. A method that, in the cardiac catheterization laboratory, allows the calculation, for example, of the pressure ratio FFR or another hemodynamic characteristic value to be ascertained, by which a decision may be made as to whether the stenosis 36 requires an invasive intervention, is provided.

The movement of the heart 24 due to the heartbeat and breathing constitutes a fundamental problem. The large number of 2D recordings or 2D projections P1, P2, P3 represent the heart 24 at different cardiac phases accordingly. Starting from the 2D projections P1, P2, P3, a calculation of the FFR-equivalent hemodynamic characteristic value FFRx is to be carried out by the analysis device.

In the angiograph 10, the volume model 30 has a particularly low proportion of movement artifacts, so the characteristic value FFRx is determined particularly accurately. For this purpose, the analysis device 14 may carry out the method explained below with reference to FIG. 2 and FIG. 3.

Figure 2:
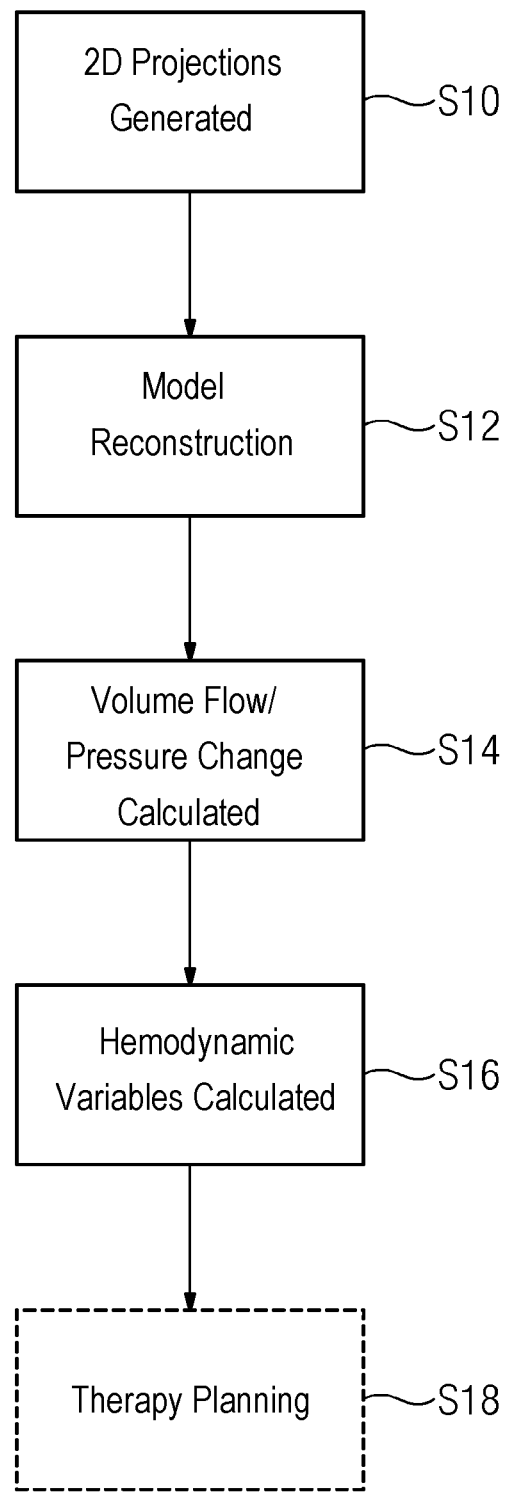
FIG. 2 shows a flow diagram for an embodiment of a method that may be carried out by the C-arm X-ray system of FIG. 1.

According to the method illustrated in FIG. 2, the 2D projections P1, P2, P3 are generated in act S10 on the specified trajectory R.

In act S12, a movement-compensated model reconstruction is carried out to obtain the described 3D reconstruction 34 of the vascular tree 32.

In act S14, the volume flow and/or a change in pressure is calculated based on the 3D reconstruction 34 (e.g., using a CFD method).

From the variables calculated hereby, the hemodynamic variables such as the described hemodynamic characteristic value FFRx may be calculated in act S16.

Therapy planning (e.g., a virtual stenting) may optionally be carried out in act S18 (e.g., a simulation SIM of a stent implantation).

Figure 3:
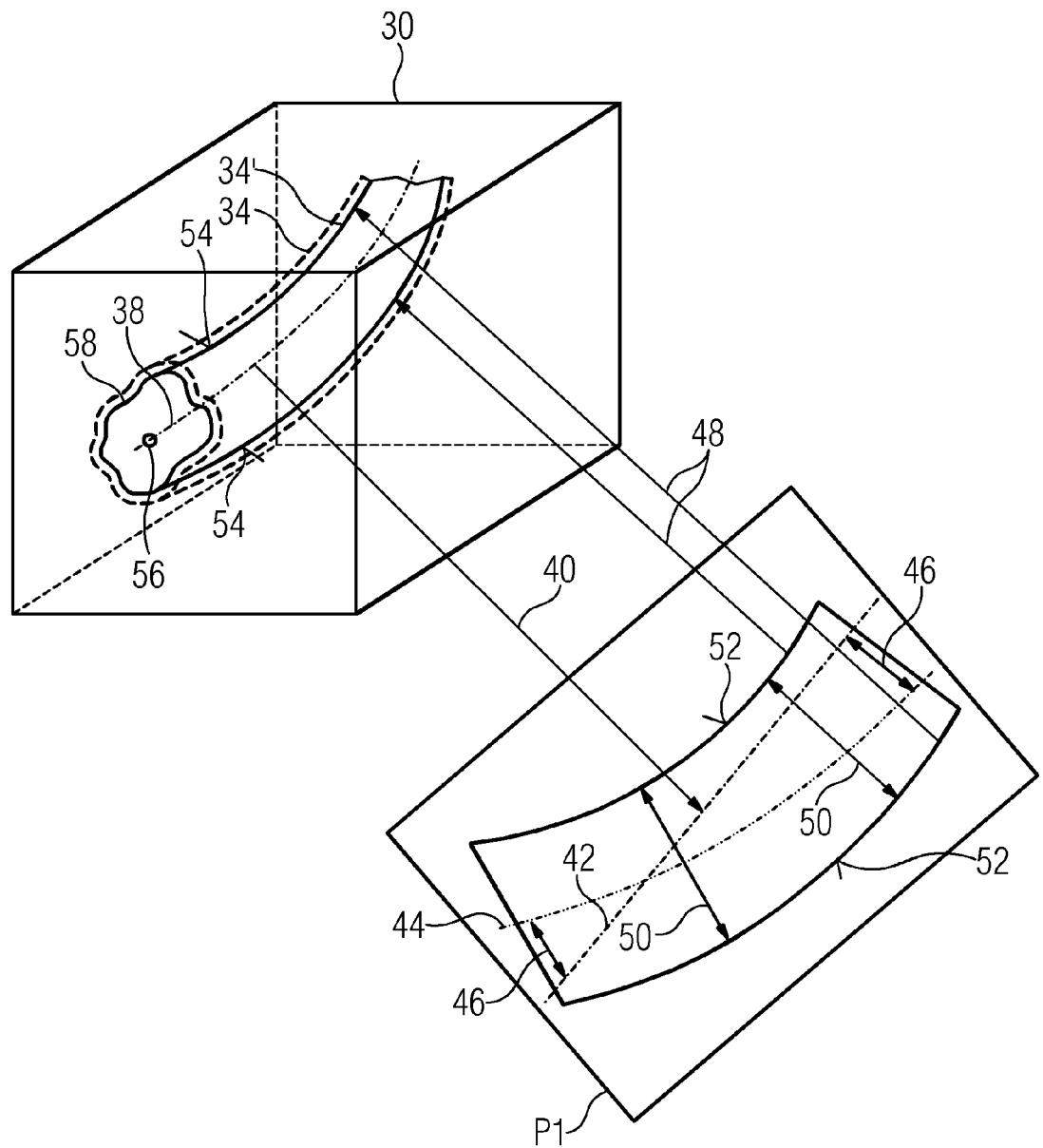
FIG. 3 illustrates a correction act that may be a part of the method of FIG. 2.

The method may be divided into two methods that differ in the estimation of the boundary conditions in act S14 for calculation of the hemodynamic variables. A first method A, which is illustrated in FIG. 3, calculates flows and pressures solely from the morphology of the blood vessels. A method B ascertains flows and pressures by taking into account the myocardial mass of the side of the heart 26 that is supplied by the blood vessel 32. Particularly good results may be obtained from a combination of the two methods A, B.

The acquisition of the large number of 2D angiographs or 2D projections P1, P2, P3 of at least one coronary artery and optionally of the supplied myocardium carried out in acts S10 and S12 may be obtained, for example, based on the methods already described, which are described in the specialist articles by Schwemmer et al.

The movement-compensated model reconstruction carried out in act S12 uses the recording data from act S10 and estimates the cardiac movement in order to compensate this movement in the image reconstruction of the model 30 to calculate a 3D image of the coronary arteries (e.g., the 3D reconstruction 34) at a predetermined cardiac phase. Heart vessels are thin structures that, owing to the direct contrasting, as may be achieved by injecting contrast medium solely into the region of the vascular tree 32, are shown very radiopaque. A rotational scan of, for example, five heartbeats are sufficient to calculate multi-segmentally the 3D structure of the vascular branch of the vascular tree 32. Two methods, for example, may be used here. The first of method is described in the document EP 2 242 023 B1. This estimates a 3D movement field in the time, and this may be used for movement compensation. In this connection, the volume of the vessels of the vascular tree 32 may be overestimated. A further method that is used for additional compensation of the respiratory movement with pre-correction is known from DE 10 2010 022 791 A1. This method estimates a 2D movement field in the time, and this is used for movement compensation.

It is to be weighed which of the two methods should be used. Simple tests with the angiograph to be implemented provide information about the suitability of the two methods.

In the model 30, the vessels of the vascular tree 32 (e.g., the 3D reconstruction 34) may be segmented by a threshold value method. There are various possibilities for threshold value segmenting. A first approach is a global threshold value that is applied to each data record. An automatically determined threshold value may take variances into account. By way of example, the threshold value may be set, such that only a precisely defined fraction of the image is segmented (e.g., 0.5% of all voxels).

The accuracy of the depiction of the volume may be increased if required by a further method, as is shown in FIG. 3.

FIG. 3 illustrates how in the model 30 the 3D reconstruction 34 shows the vascular tree 34 with an excessively large volume or diameter due, for example, to movement artifacts. The broken lines used indicate that the overestimation of the volume has been caused due to motion blur. According to the method act, the vessel diameter is sized in at least one projected image (e.g., the 2D projection P1), and then, the 3D reconstruction 34 is corrected to a 3D reconstruction 34'. This may be carried out completely automatically (e.g., automatically by the analysis device 14). A 3D center line 42, for example, is calculated from the segmented vascular tree (e.g., the 3D reconstruction 34). This 3D center line 42 is projected onto the detector images by a forward projection 40 according to the associated recording geometry. This is illustrated in FIG. 3 for the 2D projection P1. Detector images that were recorded for a cardiac phase similar to the cardiac phase of the reconstructed 3D image 34 may be selected. The forward-projected 3D center line 42 is an important aid for the 2D segmenting of the projected image P1. The projected image P1 of the coronary artery is located in the vicinity of the forward-projected 3D center line 42. The 2D center line 44 is calculated from the 2D segmenting of the coronary artery in the detector image P1. The 2D center line 44 is registered in relation to the forward-projected 3D center line 42 via a registration 46. An allocation of a point on the 2D center line 44 to a point on the 3D center line 42 is given by the forward projection 40, the 2D-2D registration 44 in the detector image P1, and a back projection 48 in the volume image (e.g., the model 30).

The diameter 50 of the coronary artery may be measured from the segmenting of the 2D detector image P1. A 3D model of an edge 52 along the 3D center line 38 may be created from the diameters 50 measured in a few 2D projected images P1, P2, P3 (e.g., the edge 54 may be ascertained in the model 30). At a specific point 56 on the 3D center line 38, the diameter may therefore be modeled along a profile line 58 parallel to a 2D projected image as the diameter 50 that was measured at the corresponding point of the 2D center line 44. The magnification due to beam expansion may be discounted. The profile line 58 results, for example, by back-projection of the edges 52 from different 2D projections P1, P2, P3.

All discussed methods may calculate a random 3D reconstruction of the coronary vessels 32 at an optimum instant with little movement. The estimated movement field may be used for 4D animation of the vascular tree 34. Due to the projection geometry, the component along the projection beam is missing in the 3D movement field from the first-mentioned method. This component may be ascertained via a periodization of the cardiac movement and use of a plurality of angles of projection in the same cardiac phase. A third component may likewise be added to the 2D movement field of the last-mentioned method via periodization of the cardiac movement and use of a plurality of projection paths in the same cardiac phase.

If a specific FFR value is to be ascertained for a defined phase position of the heartbeat, as may be the case, for example, with the characteristic value iFR known from the literature, it is advantageous to locate the choice of the instant in the specific cardiac phase. The 4D animation offers the possibility of movement analysis and movement compensation in the 2D-3D overlaying with fluoroscopy. In general, time-dependent pressure values and further hemodynamic variables in adjusted vessel geometry may be calculated.

The volume flow and/or a change in pressure is/are calculated in act S14.

According to the method A, the vessel diameter is determined at the inlet and at multiple outlets of the vascular tree 32 based on the 3D reconstruction 34. In a healthy section of the vessel, the blood flow in the vessel is proportional to the cube of the lumen diameter. If, by way of example, the mean diameter may be measured or calculated on a healthy vessel segment on a model, an estimation of the blood flow may be made thereby. The correlation between vessel and lumen diameter is optionally adapted using simple experiments. A mean maximum and minimum flow rate may also be calculated or estimated to then provide tolerance intervals in the calculation of the characteristic value FFRx. In one embodiment, a recording method with good spatial resolution may be used to determine the vessel diameter at the inlet and outlet, or outlets, as accurately as possible. The method illustrated in FIG. 3 may be used. The accuracy of the calculation of hemodynamic characteristic values is also essentially determined by the accuracy of the description of the vessel geometry that is used. The lumen diameter may also be an effective diameter (e.g., based on a double radius that is easy to ascertain and may be calculated in the case of non-round vessel cut-throughs via the cross-sectional area). Other boundary conditions may also be calculated. One example of this is the flow speed that correlates with the volume flow via the vessel diameter and the pulse.

In method B, in the difference from method A, there is an estimation of the flow that is based on the reconstruction and determination of the myocardial mass supplied by the vessel. The operation uses a measurement of the myocardial mass supplied by the vessel. The necessary blood flow may be derived from the estimation of the perfusion requirement of a typical, healthy myocardial mass, as may be found in a textbook for different genders and age groups as well. Further information such as, for example, the heart rate and possibly the blood pressure, may be used for this, and these can be measured simultaneously. The information on the myocardial mass may originate from existing advance information (e.g., a previously created CT or MR scan) or likewise be ascertained by the existing scan or a further scan with adjusted acquisition protocol. In other words, the heart 26, which is likewise depicted in the model 30, may also be measured by way of example.

A further improved possibility occurs since, due to the direct contrasting of the coronary vessels (e.g., due to the locally limited injection of contrast medium into only the blood vessel 32 to be examined), only the myocardial tissue, which is supplied by the contrasted vascular branch, is selectively depicted as well. Measurement of the supplied myocardial part is therefore possible via simple segmenting based on the model 30. In addition, the risk profile may be gauged, an undersupply may be depicted, or scar tissue may be identified with this method. An image reconstruction without movement compensation is enough to depict the myocardial area as a 3D blush. To mask or suppress image artifacts in the highly contrasted coronary artery (e.g., the vessels of the vascular tree 32 that surround the myocardium), algorithms, for example, for metal artifact reduction (MAR) may be used, or the recording profile may be changed.

The method is suitable for a large number of recording protocols. Image recording may be navigated such that both coronary vessels and the associated myocardium are contrasted. To avoid image artifacts of highly contrasted coronary arteries, two rotations may also be navigated one after the other. The coronary vessel is contrasted in the first rotation. The second rotation is coordinated such that the contrast bolus has migrated completely into the myocardial tissue, and the coronary vessels are free from contrast medium. Several possibilities exist for contrasting the vessels: contrasting may be limited locally to the individual vascular branch of the stenosis; fill a plurality of vessel segments; or detect the entire left or right coronary tree. Both coronary trees may also be contrasted, either each tree selectively or both together, systemically via an administration of contrast, for example, into the aortic root. With selective administration into the coronary trees, both trees may be contrasted simultaneously or successively. Simultaneous, selective contrasting is more invasive since two catheters are to be introduced, and therefore, two punctures are to be provided. With staggered contrasting, both coronary trees and the associated myocardial tissue are combined by image fusion. An intravenous injection may also be provided as a further option.

In act S16, a large number of methods known from the prior art may be used for the calculation of the hemodynamic characteristic values, such as of the characteristic value FFRx. One or more of the present embodiments are flexible here, therefore. Exemplary hemodynamic parameters are the local blood flow, flow speeds, flow rate, pressures and pressure differences, but also derived variables, such as characteristic values FFRx correlated with the FFR value. The pressures distally and proximally to the stenosis 36 may be suitable for calculation of FFRx. The calculation of the pressures distally and proximally to the stenosis 36 or in the entire vessel segment of the vascular tree 32 occurs by known simulation techniques. The simulation may occur using a full model, but also using reduced models that only represent the vascular tree zero-dimensionally, one-dimensionally or two-dimensionally, or using combinations of approaches. Treatment of boundary conditions using 0D and 1D models, which depict the fluidic behavior at the inflow or outflow, for example, as time characteristic values, is advantageous. The results are then used as boundary conditions in the actual two- or three-dimensional calculation in the relevant region of the vessel with stenosis 36. An iterative calculation and adjustment to the given or calculated or estimated boundary conditions may also be provided.

An adjustment of the pressures to the systemic blood pressure of the patient is advantageous for calculation of the characteristic value FFRx. The calculation of the distal and proximal pressure via the stenosis 36 initially supplies only the required pressure difference that is necessary to enable the specified blood flow. A pressure cuff, for example, on the upper arm may be used to ascertain an absolute blood pressure value. It is advantageous, however, if the patient is located in the cardiac catheterization laboratory, to ascertain the blood pressure using an invasive pressure measurement, for example, in the aorta.

In a further act, a calculation of the characteristic value FFRx may be carried out, as would correspond to a real FFR measurement (e.g., a correction is carried out since the patient is at rest during the acquisition and is not in the state of hyperemia required for the FFR measurement, as may be achieved by administration of adenosine). All data or only some may also be obtained under hyperemia. This may then also be taken into account in the calculation of the characteristic value FFRx.

Act S18 provides optional therapy planning. The highly accurate reconstruction of the geometry of the vascular tree 32 may also be used for further planning acts. This includes, for example, the implantation of a virtual stent. The user may thereby have the placement of the implant visually displayed, although the changed hemodynamic variables after implantation may also be calculated. Of interest is the calculation of the wall shear forces that may supply a possible indication of future disease and may have changed, for example, following stent implantation. The use of the 4D reconstruction may supply improved quality of results.

With the described method and the described algorithms, a hemodynamic characteristic value FFRx correlated with the FFR that, when compared to other approaches, is directly available in the cardiac catheterization laboratory and due to the integration of the specially developed, movement-compensated model reconstruction provides significantly improved accuracy, may be calculated.

In combination with the demonstrated acquisition and injection protocols, simple integration into the clinical workflow may be provided, and further improvements in the accuracy may be achieved. Further advantages compared to a CT-based method are the significantly lower requirement for contrast medium with significantly higher contrasting of the vessels at the same time.

Overall, the example shows how a virtual FFR measurement may be obtained by one or more of the present embodiments based on movement-compensated DynaCT images.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for ascertaining a fluid-dynamic characteristic value of a resilient vascular tree, through which a fluid flows in a pulsating manner, the method comprising:
generating, by a detector of a projection device, at least one two-dimensional (2D) projection, respectively, of the resilient vascular tree from different angles of projection; and
generating, by a processor, a digital three-dimensional (3D) reconstruction of the resilient vascular tree based on the 2D projections;
estimating, by the processor, a geometry of at least one vessel of the resilient vascular tree based on the digital 3D reconstruction;
ascertaining, by the processor, at least one fluid state in the resilient vascular tree from the geometry and predetermined resilient properties of the resilient vascular tree; and
calculating, by the processor, the fluid-dynamic characteristic value as a function of the at least one fluid state,
wherein the at least one fluid state comprises a fluid volume, a respective fluid pressure at at least two different instants, a respective fluid pressure at two different locations at least in the resilient vascular tree, or any combination thereof.

2. The method of claim 1, wherein the projection device comprises a C-arm angiography system.

3. The method of claim 1, wherein estimating the geometry of the at least one vessel in the 3D reconstruction comprises:
ascertaining one 3D route, respectively, of the at least one vessel;
projecting the 3D route onto one of the 2D projections; and
starting from the projected 3D route in the 2D projection, ascertaining an edge of the at least one vessel and projecting the edge back into the 3D reconstruction.

4. The method of claim 3, further comprising:
ascertaining, in the 2D projection, a 2D route of the at least one vessel; and
registering the projected 3D route and the 2D route relative to each other.

5. The method of claim 3, further comprising:
projecting the 3D route onto at least one other of the 2D projections for ascertaining a respective further edge of the at least one vessel; and
ascertaining a profile line of the at least one vessel based on all back-projected edges.

6. The method of claim 5, wherein generating the at least one 2D projection comprises generating 2D projections at a plurality of different pulse phases of a pulse cycle of the fluid that flows in a pulsating manner, and
wherein the 3D route is only projected onto the 2D projections in which a difference in the pulse phases is less than a predetermined tolerance value.

7. The method of claim 1, wherein ascertaining the at least one fluid state comprises ascertaining, starting from the geometry, the at least one fluid state using a computational fluid-dynamics method.

8. The method of claim 1, further comprising ascertaining an estimate for a quantity of fluid flowing per pulse beat based on a volume, a mass, or a combination thereof of an organ supplied with the fluid via the resilient vascular tree.

9. The method of claim 1, further comprising ascertaining an absolute fluid pressure value in the resilient vascular tree, on a vessel that fluidically communicates with the resilient vascular tree, or a combination thereof.

10. The method of claim 1, wherein calculating the fluid-dynamic characteristic value comprises ascertaining a drop in pressure in the fluid caused by a vasoconstriction of the resilient vascular tree, a value that describes a fractional flow reserve, or a combination thereof as the fluid-dynamic characteristic value.

11. The method of claim 1, further comprising:
simulating a manipulation of the resilient vascular tree in the 3D reconstruction; and
predicting a manipulation-induced fluid-dynamic characteristic value with the aid of the simulation.

12. A C-arm X-ray system comprising:
a projection unit comprising:
an X-ray source configured to penetrate a vascular tree in a body; and
an X-ray detector configured to generate two-dimensional (2D) projection data of 2D projections of the penetrated vascular tree; and
an analysis device configured to:
generate a digital three-dimensional (3D) reconstruction of the vascular tree based on the 2D projections;
estimate a geometry of at least one vessel of the vascular tree based on the digital 3D reconstruction;
ascertain at least one fluid state in the vascular tree from the geometry and predetermined resilient properties of the vascular tree; and
calculate a fluid-dynamic characteristic value as a function of the at least one fluid state,
wherein the at least one fluid state comprises a fluid volume, a respective fluid pressure at at least two different instants, a respective fluid pressure at two different locations at least in the resilient vascular tree, or any combination thereof.

13. The C-arm X-ray system of claim 12, wherein the projection device comprises a C-arm angiography system.

14. The C-arm X-ray system of claim 12, wherein the estimation of the geometry of the at least one vessel in the 3D reconstruction comprises:
ascertainment of one 3D route, respectively, of the at least one vessel;
projection of the 3D route onto one of the 2D projections; and
starting from the projected 3D route in the 2D projection, ascertainment of an edge of the at least one vessel and projecting the edge back into the 3D reconstruction.

15. The C-arm X-ray system of claim 14, wherein the analysis device is further configured to:
ascertain, in the 2D projection, a 2D route of the at least one vessel; and
register the projected 3D route and the 2D route relative to each other.

16. A method for ascertaining a fluid-dynamic characteristic value of a resilient vascular tree, through which a fluid flows in a pulsating manner, the method comprising:
generating, by a projection device, at least one two-dimensional (2D) projection, respectively, of the resilient vascular tree from different angles of projection;
generating, by a processor, a digital three-dimensional (3D) reconstruction of the resilient vascular tree based on the 2D projections;
estimating, by the processor, a geometry of at least one vessel of the resilient vascular tree based on the digital 3D reconstruction;
ascertaining, by the processor, at least one fluid state in the resilient vascular tree from the geometry and predetermined resilient properties of the resilient vascular tree;
calculating, by the processor, the fluid-dynamic characteristic value as a function of the at least one fluid state;
simulating a manipulation of the resilient vascular tree in the 3D reconstruction; and
predicting a manipulation-induced fluid-dynamic characteristic value with the aid of the simulation.

17. A method for ascertaining a fluid-dynamic characteristic value of a resilient vascular tree, through which a fluid flows in a pulsating manner, the method comprising:
generating, by a projection device, at least one two-dimensional (2D) projection, respectively, of the resilient vascular tree from different angles of projection;
generating, by a processor, a digital three-dimensional (3D) reconstruction of the resilient vascular tree based on the 2D projections;
estimating, by the processor, a geometry of at least one vessel of the resilient vascular tree based on the digital 3D reconstruction, the estimating of the geometry of the at least one vessel in the digital 3D reconstruction comprising ascertaining a 3D route, respectively, of the at least one vessel, projecting the 3D route onto one of the 2D projections, and starting from the projected 3D route in the 2D projection, ascertaining an edge of the at least one vessel and projecting the edge back into the 3D reconstruction;
ascertaining, by the processor, at least one fluid state in the resilient vascular tree from the geometry and predetermined resilient properties of the resilient vascular tree;
calculating, by the processor, the fluid-dynamic characteristic value as a function of the at least one fluid state;
projecting the 3D route onto at least one other of the 2D projections for ascertaining a respective further edge of the at least one vessel; and
ascertaining a profile line of the at least one vessel based on all back-projected edges,
wherein generating the at least one 2D projection comprises generating 2D projections at a plurality of different pulse phases of a pulse cycle of the fluid that flows in a pulsating manner, and
wherein the 3D route is only projected onto the 2D projections in which a difference in the pulse phases is less than a predetermined tolerance value.

* * * * *